United States Patent [19]
Goll

[11] Patent Number: 6,145,506
[45] Date of Patent: Nov. 14, 2000

[54] DECORATIVE PENILE WRAP

[76] Inventor: Dawn M. Goll, 983 Watson, Saline, Mich. 48176

[21] Appl. No.: 09/059,747

[22] Filed: Apr. 14, 1998

[51] Int. Cl.[7] .................................................. A61F 6/04
[52] U.S. Cl. ........................................... 128/844; 128/918
[58] Field of Search ..................... 128/842, 844, 128/918; 604/347–353; 600/38–41

[56] References Cited

U.S. PATENT DOCUMENTS

| | | | |
|---|---|---|---|
| 3,939,827 | 2/1976 | Brunstetter | 600/38 |
| 4,523,584 | 6/1985 | Yachia | 600/38 |
| 5,238,009 | 8/1993 | House | 128/842 |
| 5,331,974 | 7/1994 | Sook | 128/844 |
| 5,454,379 | 10/1995 | Shepherd | 128/844 |
| 5,524,638 | 6/1996 | Lyons | 128/844 |

*Primary Examiner*—Michael A. Brown
*Attorney, Agent, or Firm*—Young & Basile, PC

[57] ABSTRACT

A decorative penile wrap encircles a human male penis. The decorative penile wrap is in the form of a cylindrical sheath having a hollow interior and opposed, open, first and second ends. A fastener is provided in one embodiment for securing opposed side edges of the sheath together to form a planar sheet into a cylindrical sheath. Decorative indicia is formed on the exterior of the sheath to provide a stimulating appearance. Alternately, the sheath is formed with a continuous, closed side wall.

19 Claims, 3 Drawing Sheets

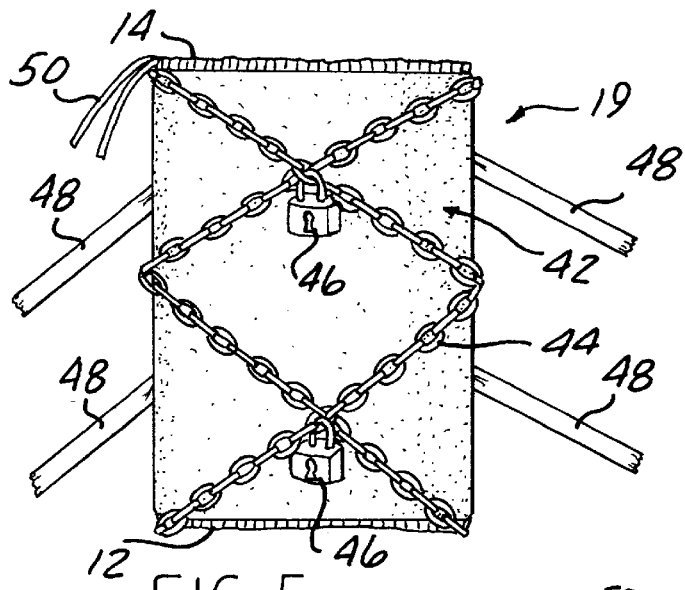
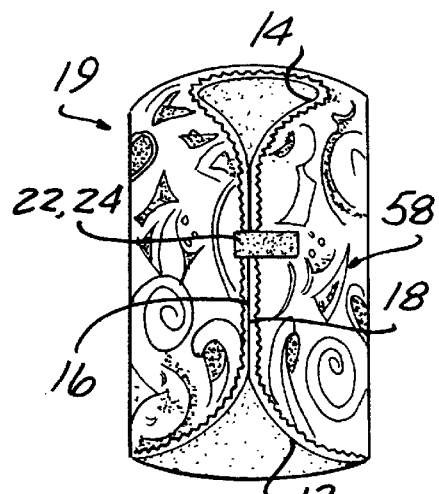
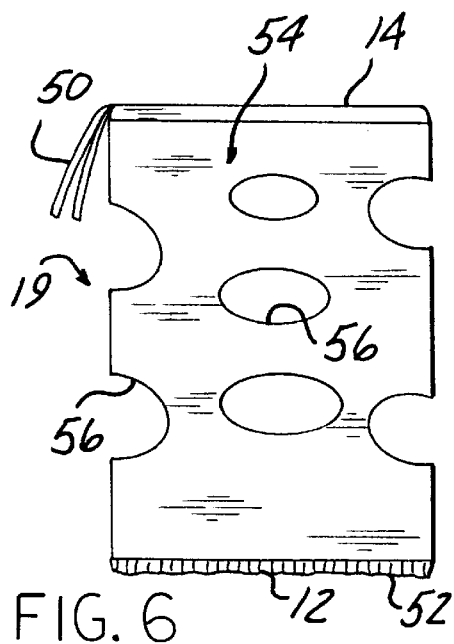
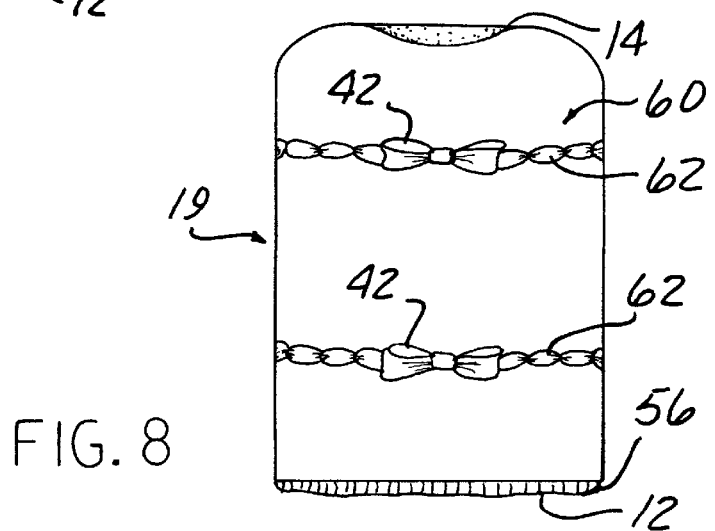

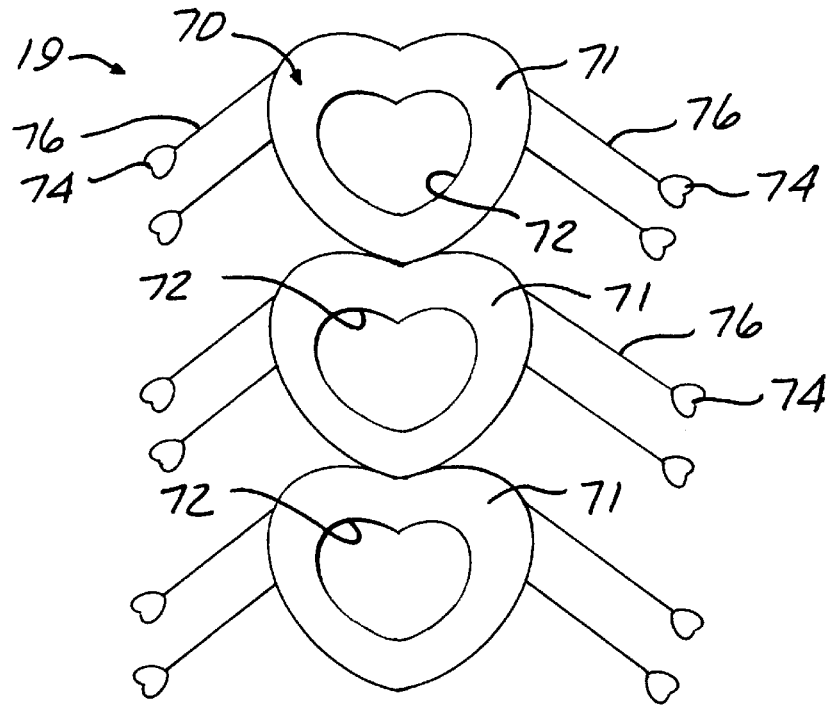
FIG. 9
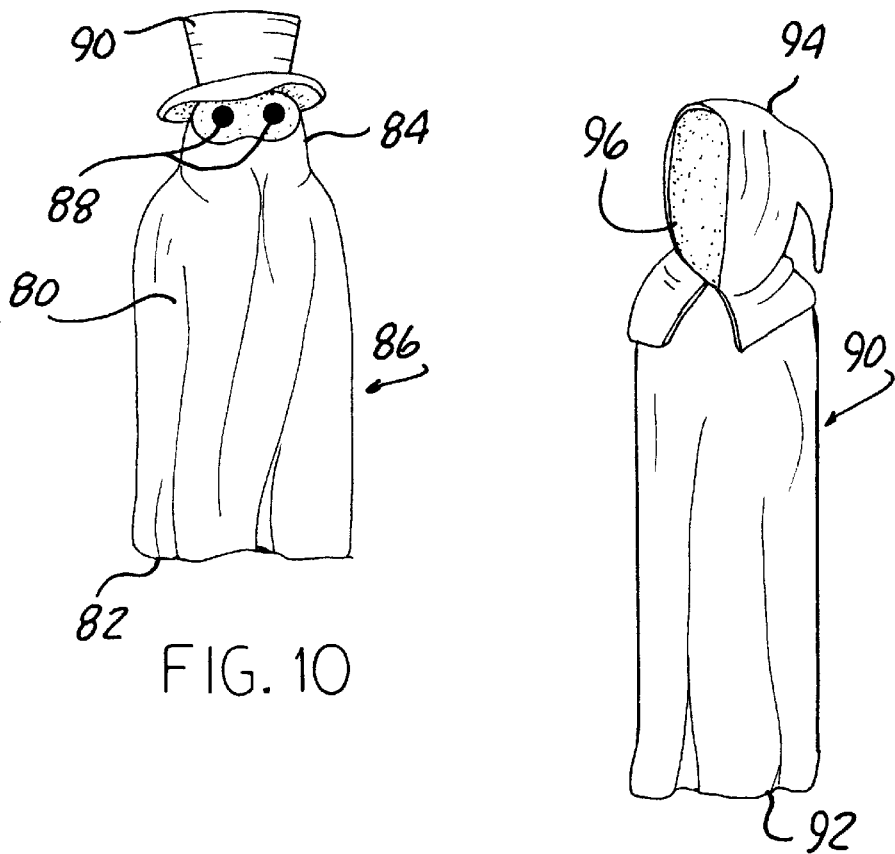
FIG. 10
FIG. 11

DECORATIVE PENILE WRAP

BACKGROUND OF THE INVENTION

1. Field of the Invention

The present invention relates, in general, to sexual devices.

2. Description of the Art

Prior to and during sexual intercourse, humans typically engage in foreplay to heighten sexual arousal of both the male and female. In addition to physical contact or touching, humans have also employed various devices to heighten sexual arousal by appealing to some or all of the other human senses.

For example, sheer lingerie is widely used for its visual appearance and feel. The important role that imagination plays in sexual arousal has led to the use of costumes and role playing. Other devices are used to stimulate certain body parts, either prior to, during, or in lieu of actual intercourse.

Condoms, while typically employed to prevent pregnancy or the transmittal of sexual diseases, have also been used as a means of heightening sexual arousal through the provision of ribs, colors, flavors, or glow-in-the dark pigments.

While such devices have been pleasurably used by many humans, it would still be desirable to provide a device which can be used prior to sexual intercourse to heighten the sexual arousal of both the male and female. It would also be desirable to provide such a device which can be easily applied to a male penis. It would also be desirable to provide such a device with various decorative features which have a stimulating significance to a particular couple.

SUMMARY OF THE INVENTION

The present invention is a decorative penile wrap which is applied in an encircling manner about a human male penis to provide a stimulating appearance to heighten sexual arousal of a male and female prior to intercourse or other sexual activity.

The decorative penile wrap includes a sheath means for encircling the penis, the sheath means having a side wall extending between first and second ends and forming a hollow interior bore. Means are provided for securing the sheath about a human penis. Decorative indicia is formed on the exterior of the side wall of the sheath means to provide a stimulating appearance.

The securing means may take a variety of forms including an elastic band, tie straps, Velcro-type fasteners, or other suitable fasteners mounted at one or more locations along the length of the side edges of the sheet forming the sheath means or at one or both of the ends of the sheath means.

In a preferred embodiment, each of the first and second ends of the sheath means is open. The sheath means may also be formed with a continuous, closed side wall.

The decorative indicia can take a variety of different forms, and may be provided in any form which a particular couple finds to be particularly stimulating.

The decorative indicia may be in the form of a two or three dimensional applique fixedly mounted on the exterior of the side wall of the sheath means. Alternately, the decorative indicia may be a design printed or otherwise applied to the exterior side wall of the sheath means. The sheath means may also be formed into a particular shape or design.

By way of example, the decorative indicia may be in the form of an inanimate object such as a simulated snowman, golf bag, shirt or other article of clothing, a ghost, the grim reaper, etc. The decorative indicia can also be in the form of simulated animate objects, such as an animal. Finally, the decorative indicia can be a decorative design applied to the side wall of the sheath means.

The decorative penile wrap of the present invention provides a unique device which may be used to heighten the sexual arousal of a human male and female prior to sexual intercourse or other sexual activity. The decorative penile wrap is designed to encircle a male penis, and is provided with decorative indicia which presents a stimulating appearance to a male and female. The decorative penile wrap is easy to use and may be provided in a number of different configurations including different decorative designs to suit the desires of a particular couple.

BRIEF DESCRIPTION OF THE DRAWINGS

The various features, advantages and other uses of the present invention will become more apparent by referring to the following detailed description and drawing in which:

FIG. 5 is a plan view of yet another embodiment of the decorative penile wrap of the present invention;

FIG. 6 is a plan view of yet another embodiment of the decorative penile wrap of the present invention;

FIG. 7 is a bottom view of yet another embodiment of the decorative penile wrap of the present invention;

FIG. 8 is a plan view of yet another embodiment of the decorative penile wrap of the present invention;

FIG. 9 is a plan view of yet another embodiment of the decorative penile wrap of the present invention;

FIG. 10 is a plan view of yet another embodiment of the decorative penile wrap of the present invention; and FIG. 11 is a plan view of yet another embodiment of the decorative penile wrap of the present invention.

DESCRIPTION OF THE PREFERRED EMBODIMENTS

Figure 1:
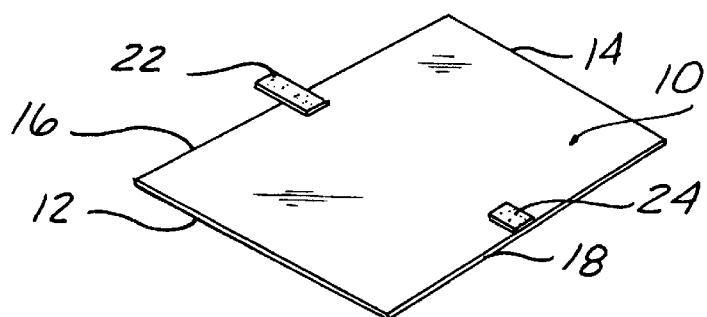
FIG. 1 is a perspective view of one embodiment of a decorative penile wrap constructed in accordance of the teachings of the present invention.

Referring now to the drawings, there is depicted a decorative penile wrap which is applied about a human male penis for decorative purposes. The decorative wrap is particularly intended to heighten the sexual arousal of a male and female prior to sexual intercourse.

Figure 2:
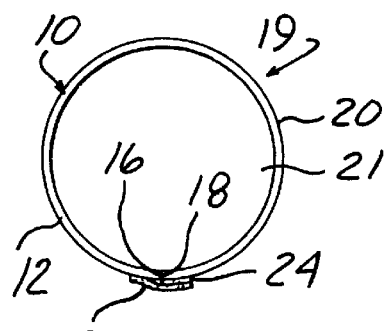
FIG. 2 is an end view of the decorative penile wrap shown in FIG. 1, formed into its use shape.

Referring in detail to FIGS. 1 and 2, there is depicted a planar sheet 10 which is used to form one embodiment of the decorative penile wrap of the present invention. The planar sheet 10, which may have any suitable size, is formed with opposed first and second ends 12 and 14 and opposed first and second side edges 16 and 18. The size of the material sheet 10 is selected such that the sheet 10, when folded into a generally tubular, cylindrical sheath 19, as shown in FIG. 2, with a side wall 20 and an interior bore 21 sized to fit about and encircle a male penis.

The sheet 10 may be provided with any suitable length between the opposed first and second ends 12 and 14, respectively. Preferably, however, the length of the sheet 10 between the opposed first and second ends 12 and 14 is selected such that the sheet 10, when applied about a penis will extend substantially between the base of the shaft of the penis to behind the glans.

The sheet 10 may be formed of any suitable material. Preferably, the material is washable and, even more preferable, the material is a flexible, soft fabric. The fabric may be either natural or man made, such as cotton, rayon, silk, by way of example only. The sheet 10 may also be formed of courser materials including rigid or semi-rigid materials, such as leather.

The decorative penile wrap of the present invention also includes means for securing the sheet 10, when formed into a sheath 19, as shown in FIG. 2, about a male penis. The securing means may be provided in any one of a number of different closures or fasteners. As shown in FIGS. 1 and 2, a first fastener used on the decorative wrap of the present invention is a Velcro-type fastener formed of interconnecting hook and mesh members 22 and 24 which are securely mounted, such as by adhesive, stitching, etc., to the opposite side edges 16 and 18 of the sheet 10. When the sheet 10 is formed into the sheath 19, as shown in FIG. 2, the members 22 and 24 interlock to securely retain the sheet 10 in a sheath-like shape about a male penis. It will be understood that the intermeshing members 22 and 24 may be provided at a single location along the length of the sheet 10, as shown in FIG. 1, or at multiple spaced locations along the length of the sheet 10 or may be provided in continuous strips extending along at least a portion of or substantially all of the side edges 16 and 18 of the sheet 10.

When formed into the sheath 19, the ends 12 and 14 form apertures opening to the bore 21 extending through the sheath 19.

As described hereafter in conjunction with various embodiments of the present invention, the securing means may also be in the form of tie straps which are mounted on each side edge 16 and 18 and extend loosely outward therefrom. The tie straps are tied or knotted together to secure the sheet 10 in a sheath-like shape 19. Elastic bands may also be formed at one or both ends of the sheath 19. Further, a combination of a tie strap at one end and an elastic band at the other end of the sheath 19 may also be employed. In addition, other types of fasteners, not shown, which may be used with the present decorative wrap include a zipper, snaps, buttons and interengagable hooks mounted on the opposed side edges 16 and 18 of the sheet 10. Alternately, adhesive may be applied to the opposed side edge positions for a single use, disposable decorative wrap.

Figure 3:
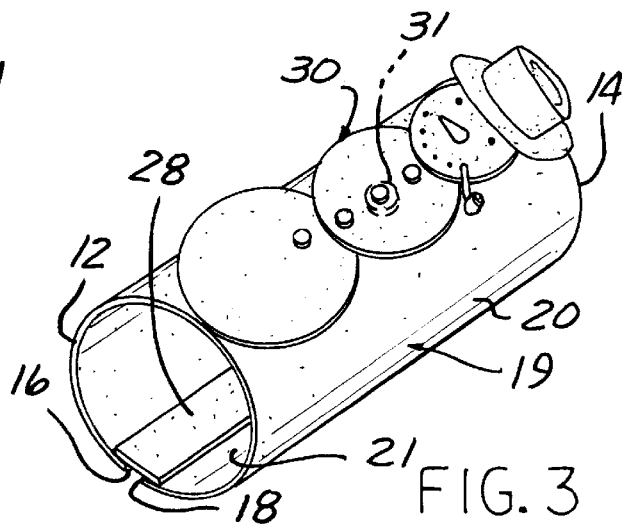
FIG. 3 is a perspective view of another embodiment of the decorative penile wrap of the present invention.

Further, as shown in FIG. 3, a single elongated elastic strip 28 may be permanently secured to the opposed side edges 16 and 18 of the sheath 19, with the elastic strip 28 extending along at least a portion of the length of the sheath 19. This retains the sheath 19 permanently in the cylindrical shape shown in FIG. 3.

The embodiment shown in FIG. 3 suggests a variation to the decorative penile wrap in which the sheath 19 is formed of a single continuous sheet having a continuous side wall 20 or a side wall 19 with two permanently connected side edges 16 and 18 so as to cause the sheath 19 to permanently remain in the cylindrical shape shown in FIG. 3. This continuous tubular shape lends itself to the use of stretchable or elastic materials in forming the sheet 10. The use of such elastic materials, elastic bands and the other adjustable closures described above, including the tie straps and Velcro-type fasteners, provide an additional advantage in that the diameter of the sheath 19 can be small or adjusted to be small so as to provide the selected amount of tightness in use.

A unique feature of the decorative penile wrap of the present invention is the provision of decorative indicia denoted generally by reference number 30 in the embodiment shown in FIG. 3. The purpose of the decorative indicia 30 is to appeal to the sense of sight and the imagination of the users, especially where the decorative indicia may have some significance or meaning to the user(s).

The decorative indicia 30 may be in the form of applique which is fixedly mounted on the exterior of the side wall 20 of the sheath 19. The decorative indicia 30, when provided in the form of an applique, may have a generally flat two dimensional shape or, preferably, a three dimensional shape.

The decorative indicia 30 may also be applied, by printing, painting, etc., directly on the exterior of the side wall 20 of the sheath 19 in any desired pattern. In addition, when the sheet 10 is formed of a fabric, the decorative indicia 30 can be woven in the desired pattern or design directly in the fabric.

Various examples of the decorative indicia used in the decorative wrap of the present invention will now be described in conjunction with FIGS. 3–11. It will be understood that such decorative indicia are by way of example only and are not meant to limit the particular decorative indicia employed on the decorative wrap of the present invention.

As shown in FIG. 3, the decorative indicia 30 is in the form of a three dimensional snowman having a hat and facial features normally found in a snowman. The decorative indicia 30 is mounted on the exterior of the side wall 20 of the sheath 19 by means of a suitable adhesive or by stitching. In the particular configuration shown in FIG. 3, the decorative indicia 30 has a length substantially the same as the length of the sheath 19 between the first and second ends 12 and 14, with the hat extending outward from the second end 14.

As further shown in FIG. 3, the securing or closure means is in the form of the elastic strip 28 permanently secured to the side edges 16 and 18 of the sheet 10 and extending along the entire length of the sheet 10 to permanently form the sheet 10 into the cylindrical-shaped sheath 19.

In use, the decorative wrap is applied over a penis by pulling the sheath 19 from the first end 12 over the penis until the first end 12 is located substantially adjacent the base of the penis. The length of the sheath 19 is selected such that the glans of the penis extend outward through the open second end 14 of the sheath 19. Alternately, the length of the sheath 19 may be selected such that the sheath 19 covers the entire glans of the penis.

FIG. 3 also illustrates another optional feature of the present invention. As shown therein, a small housing 31 is mounted within the applique 30, the housing 31 has a size approximate the size of a conventional watch battery and houses a conventional sound playback device containing on-board logic, non-volative memory, a power source and a push button, such as the ISD1100 sold by Information Storage Devices, San Jose, Calif. The memory stores voice and/or audio signals in analog form to generate a familiar song, such as Happy Birthday, Merry Christmas, etc., animal or human sounds or a voice phrase. When activated by depression of the push button, which can be located directly below the simulated button on the snowman shown in FIG. 3, the sound playback device accesses the analog data stored in the memory and generates the programmed musical notes or sounds which are broadcast externally from the enclosure 31. This can be used to provide additional excitement for a couple particularly if the musical notes or song have a particular meaning to the couple or are related in some fashion to the particular design or applique applied to the sheath 19.

Figure 4:
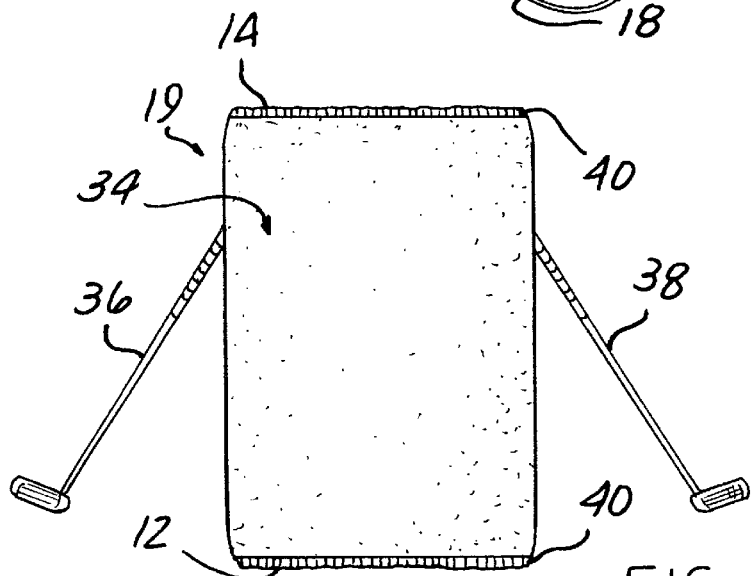
FIG. 4 is a plan view of another embodiment of the decorative penile wrap of the present invention.

In FIG. 4, the sheath 19 having a continuous cylindrical shape is formed with decorative indicia in the form of a golf bag 34. The golf bag 34 is provided with suitable indicia on the exterior surface to simulate a conventional golf bag. A pair of flexible straps 36 and 38 extend outward from the main portion of the golf bag 34 and are in the form of golf clubs, such as a golf putter. Elastic bands denoted by reference number 40 are secured within folded over end portions at the first and second ends 12 and 14 of the sheath 19. It will also be understood that the sheath 19 shown in FIG. 4 may be provided with only a single elastic band 40 at either of the first or second ends 12 and 14.

Referring now to FIG. 5, there is depicted a sheath 19 which is provided with exterior decorative indicia 42 in the form of a bodyshirt, complete with real or simulated chains 44 and locks 46. In addition flexible leather or simulated leather straps 48 extend outward from the sheath 19. A tie strap 50 may be formed in a folded over portion at the second end 14 of the sheath 19, with the ends of the strap 20, after being pulled to the desired degree of tightness, secured together by means of a knot or bow to retain the sheath 19 in position.

FIG. 6 depicts another embodiment of the present invention in which the sheath 19 is formed with decorative indicia 54 in the form of a simulated leather bodyshirt with a plurality of openings or holes 56 formed therein. This embodiment depicts a combination of different securing means including a tie strap 50 at the second end 14 of the sheath 19 and an elastic band 52 at the first end 12 of the sheath 19.

FIG. 7 depicts yet another embodiment of the decorative wrap of the present invention in which the sheath 19 is formed with curved ends 12 and 14 which, when the side edges 16 and 18 are joined together by means of a suitable fastener, such as a Velcro-type fastener 22, 24, simulate a vest or blouse. The decorative indicia 58 in this embodiment is in the form of a design imprinted on the exterior surface of the side wall 20 of the sheath 19.

FIG. 8 depicts another embodiment of the sheath 19 in which decorative indicia 60 in the form of a pair of ribbons 62 are attached to or formed on the side wall 20 of the sheath 19. Each ribbon 62 is tied in a bow 64. While the ribbons 62 may be used to form the securing means for mounting of the sheath 19, FIG. 8 depicts an elastic band 56 mounted on the first end 12 of the sheath 19. The second end 14 of the sheath 19 may be provided without any securing or fastener means or with any of the securing means described above.

FIG. 9 depicts another embodiment of the decorative wrap of the present invention. In this embodiment, the sheet used to form the sheath 19 is formed with decorative indicia 70 in the shape of overlapping hearts 71. Apertures 72 may be formed in each heart 71. In addition, smaller hearts 74 extend outward from and are attached to each larger heart 71 by means of thin strings 76. A number of small hearts 74 may be thus secured to each large heart 71 as shown in FIG. 9. The strings 76 may be used to form the securing means or may be provided solely for decorative purposes.

An alternate embodiment of the decorative wrap of the present invention is shown in FIG. 10. In this embodiment, a sheet 80 has its opposed side edges and one end closed by means of stitching or other suitable means to form a generally cylindrical shape with a first open end 82 and an opposed, closed second end 84. This arrangement forms a generally loose or billowy shape to the sheath 86. Decorative indicia in the form of eyes 88 and a hat 90 may be formed on the closed end 84 of the sheet 80 to simulate a ghost. The first end 82 may be provided with any of the aforementioned securing means, preferably an elastic band or tie strap, for secure mounting of the sheath 86.

In the embodiment shown in FIG. 11, a cylindrical sheath 90 is formed with an open first end 92 and a closed second end 94. The closed second end 94 is formed by a hood-like shape attached to the tubular sheath 90. An opening 96 formed in the hood simulates a grim reaper.

Other examples of decorative indicia which may be employed on the decorative penile wrap of the present invention, while not shown, may include any design or shape, such as a tuxedo with top hat, a flowing cape, etc. Further, artificial or natural gemstones, such as diamonds, rubies, etc., may be incorporated into any of the decorative indicia described above or such gemstones may be arranged to form a particular design on the decorative wrap.

In summary, there has been disclosed a unique decorative penile wrap which encircles a human male penis to provide a stimulating visual appearance to heighten sexual arousal of a male and female. Further, the decorative penile wrap may be provided with a large variety of exterior decorative indicia to provide a stimulating appearance, particularly when the indicia has a particular significance to a couple.

What is claimed is:

1. A decorative penile wrap mountable about a human penis for stimulative, non-intercourse use comprising:

a sheath sized for encircling a human penis, the sheath having a cylindrical wall extending between opposed, first and second open ends, the cylindrical wall forming a hollow interior bore for receiving a human penis, the cylindrical wall disposed substantially in contact with the penis along the entire length of the wall;

means for securing the sheath about a human penis; and decorative indicia formed on the exterior of the wall of the sheath;

the wall of the sheath and the decorative indicia forming a three dimensional, stimulative shape requiring removal of the sheath for intercourse.

2. The decorative penile wrap of claim 1 wherein:

the decorative indicia is in the form of an applique attached to an exterior surface of the wall of the sheath.

3. The decorative penile wrap of claim 1 wherein:

the decorative indicia is imprinted on the exterior exterior of the wall of the sheath.

4. The decorative penile wrap of claim 1 wherein:

the decorative indicia is a predetermined shape formed in the wall of the sheath.

5. The decorative penile wrap of claim 1 wherein the securing means comprises:

an elastic band fixedly mounted on at least one of the first and second ends of the sheath, the at least one of the first and second ends having a continuous periphery.

6. The decorative penile wrap of claim 1 wherein the securing means comprises:

tie straps mounted on at least one of the first and second side edges of the sheath and joinable together.

7. The decorative penile wrap of claim 1 wherein:

the first and second side edges of the sheath are disposed in proximity with each other, the securing means mounted on the first and second side edges.

8. The decorative penile wrap of claim 7 wherein the securing means comprises:

at least one tie strap secured to each of the first and second side edges of the sheath.

9. The decorative penile wrap of claim 8 wherein the securing means comprises:

interconnectible fastener elements, mounted on each of the first and second side edges of the sheet and joinable together.

10. The decorative penile wrap of claim 1 wherein:

the sheath is formed of a flexible material.

11. The decorative penile wrap of claim 1 wherein:

the sheath is formed of a semi-rigid material.

12. The decorative penile wrap of claim 1 wherein:

the securing means is mounted on each of the first and second ends of the sheath.

13. The decorative penile wrap of claim 12 wherein the securing means comprises:

elastic formed in the sheath for allowing expansion of a diameter of the sheath.

14. The decorative penile wrap of claim 1 wherein:

the sheath is formed with a continuous cylindrical shaped side wall.

15. The decorative penile wrap of claim 1 wherein:

the securing means is mounted on at least one of the first and second ends of the sheath.

16. The decorative penile wrap of claim 1 further comprising:

means, mounted on the side wall of the sheath, for generating, when activated, a series of audible sounds stored in a memory.

17. The decorative penile wrap of claim 1 wherein:

the decorative indicia defines a three dimensional shape over the entire exterior surface of the sheath.

18. The decorative penile wrap of claim 1 wherein:

the securing means forms part of the decorative indicia.

19. The decorative penile wrap of claim 1 wherein the decorative indicia includes flexible straps loosely extending from the sheath.

* * * * *